United States Patent [19]

Sleeter et al.

[11] Patent Number: 4,784,738

[45] Date of Patent: Nov. 15, 1988

[54] APPARATUS AND METHOD FOR GEL CASTING

[75] Inventors: Donald D. Sleeter, Berkeley; George G. Fernwood, San Anselmo; Samuel Burd, Oakland, all of Calif.

[73] Assignee: Bio-Rad Laboratories, Inc., Hercules, Calif.

[21] Appl. No.: 808,307

[22] Filed: Dec. 12, 1985

[51] Int. Cl.$^4$ .................... G01N 27/28; G01N 27/26
[52] U.S. Cl. .................... 204/182.8; 204/299 R; 204/180.1
[58] Field of Search .............. 204/182.8, 299 R; 156/DIG. 108

[56] References Cited

U.S. PATENT DOCUMENTS

| | | | |
|---|---|---|---|
| 3,129,158 | 4/1964 | Raymond et al. | 204/182.8 |
| 3,407,133 | 10/1968 | Oliva et al. | 204/182.8 |
| 3,751,357 | 8/1973 | Rains | 204/299 R |
| 3,773,646 | 11/1973 | Mandle et al. | 204/299 R |
| 3,855,111 | 12/1974 | Allington | 204/182.1 |
| 3,879,280 | 4/1975 | Peterson et al. | 204/299 |
| 4,111,784 | 9/1978 | Dahms | 204/182.8 |
| 4,290,871 | 9/1981 | Hoefer et al. | 204/182.8 |
| 4,325,796 | 4/1982 | Hoefer et al. | 204/182.8 |

Primary Examiner—John F. Niebling
Assistant Examiner—John S. Starsiak, Jr.
Attorney, Agent, or Firm—Townsend and Townsend

[57] ABSTRACT

A gel used for electrophoresis is cast in a gel enclosure in which the gel will ultimately be used during the electrophoresis, by a novel method and using novel apparatus which provide for quick assembly and avoidance of leaks. The method and apparatus involve a wettable, preferably porous, membrane such as filter paper, which is thoroughly wetted with gel forming solution, then placed over the bottom opening of the gel enclosure and held in place until the gel on the membrane sets. Sealing of any cracks, gaps or irregularities along the rim of the opening is thereby achieved by the capillary action of the gel forming solution. The enclosure itself is then filled with gel forming solution. Once the latter has set, the membrane is removed.

10 Claims, 1 Drawing Sheet

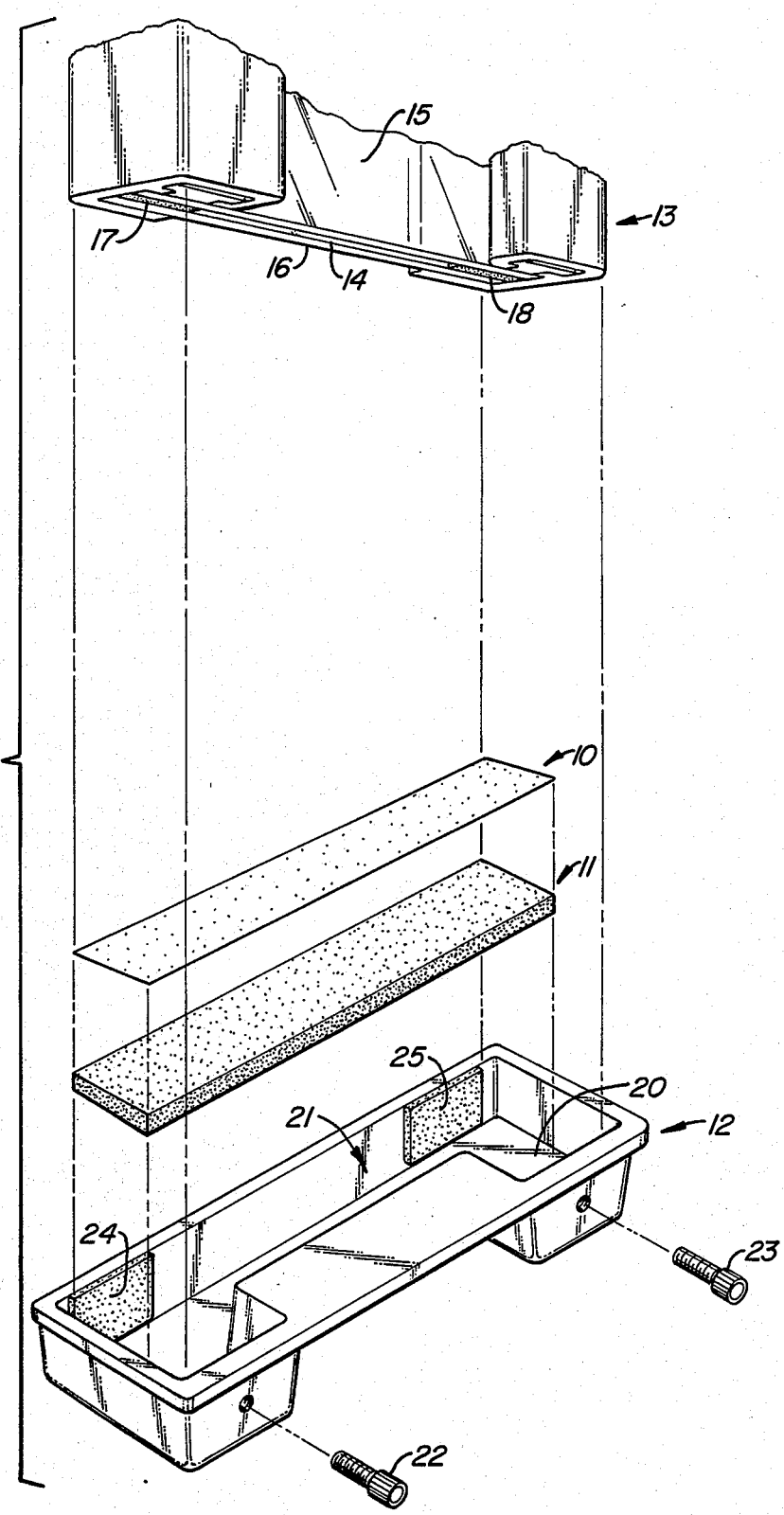
FIG._1.

APPARATUS AND METHOD FOR GEL CASTING

BACKGROUND OF THE INVENTION

This invention relates to preparation of electrophoresis gels.

Electrophoresis gels are generally cast by the user in the same enclosures in which they are held during the actual electrophoresis. When electrified buffer solutions are used to apply the potential across the gel, the enclosure must be open at each of two opposing ends to expose the gel to each solution. To cast the gel, of course, one of these open ends must be sealed off so that the gel forming solution can be added and held inside until it sets to form the gel.

In many cases among the many sizes and geometries of electrophoresis gels, it is a simple matter to seal off one of the two openings in such a manner that will prevent leakage and yet permit easy removal once the gel is cast. In others, however, this presents a problem, particularly when the enclosures comprise several parts clamped together. Slab gel enclosures consisting of a pair of flat plates separated by spacers are a prime example. DNA sequencing cells are particularly troublesome, since the plates are large and dimensionally inexact. The plates are made of glass, beveled at the edges to resist chipping. Both the size and the beveled edges make them difficult to align accurately. When poorly aligned plates are clamped together with spacers in between, commonly used casting stands equipped with gaskets are generally insufficient to establish a water tight seal at the lower end of the plates.

One alternative has been the use of sealing tape across the opening. This is difficult and time consuming, however, and runs the risk of contaminating the gel solution with the tape adhesive. Another alternative has been to insert a third spacer between the plates along the bottom edge. This results in a recessed gel, however, which is capable of entrapping air bubbles due to incomplete evacuation prior to electrophoresis, and of retaining air bubbles generated by the electrode during the electrophoresis itself.

SUMMARY OF THE INVENTION

A novel method and apparatus for sealing the lower opening of a gel enclosure are provided herein, which overcome the problems enumerated above. In accordance with this invention, a wettable membrane soaked in gel forming solution is applied to the opening and held in place until the gel in the solution sets. Prior to setting, the solution flows by capillary action to fill all voids and irregularities along the bottom edge of the enclosure. The gel upon setting thus completely seals the opening. Gel forming solution for the bulk of the gel may then be poured in through the upper opening, with leakage at the bottom prevented by the preset gel at the membrane surface. Once the entire gel has been set, the membrane may be manually removed, leaving both opposing edges of the gel exposed. The process is quick and efficient, since alignment of the enclosure plates is no longer critical and voids are filled and sealed by capillary attraction.

BRIEF DESCRIPTION OF THE DRAWINGS

The FIGURE associated herewith is an exploded view in perspective of one embodiment of the present invention, showing a slab-type gel enclosure, a wettable membrane sized to close the bottom opening of the enclosure, and associated parts for holding the two together during the sealing of the opening and casting of the gel.

DETAILED DESCRIPTION OF THE INVENTION AND PREFERRED EMBODIMENTS

The components shown in the FIGURE include the wettable membrane 10, a foam pad 11 as back-up support, a supporting tray 12, and the gel enclosure 13. The bottom opening 14 of the gel enclosure is defined by a pair of flat glass plates 15, 16, separated along their side edges by a pair of spacer strips 17, 18. The rim of the opening is defined by the exposed lower edges of the glass plates and the exposed lower ends of the spacer strips.

The membrane 10 is large enough to overlap the entire rim, thereby closing off the opening 14 entirely.

The membrane must be wettable and sufficiently flexible to conform to any irregularities along the rim such as misaligned or chipped parts. In preferred embodiments, the membrane is made of a porous material to retain gel-forming solution inside it as well as on the surface. Preferred materials are also those which are capable of easy and complete removal from the rim once the gel has set, and thus should not tear when pulled off by hand. Within these considerations, the actual material itself is not critical and may include a broad range of substances. Examples are plastics, papers, fabrics, thin fine sponges and fine gauzes provided they are wettable by the gel-forming liquid. In the case of porous materials, the membrane should be fully saturated with gel-forming liquid prior to placement against the rim. Paper is preferred, particularly smooth filter paper (rather than creped) having a water absorbency ranging from about 1 to about 6 grams per 100 square centimeters, and a wet strength of at least about 25 psi. One example of such paper is laboratory filter paper having a water absorbency of 5 grams per 100 square centimeters and a wet strength of 30 psi.

The thickness of the membrane is not critical, although it may be a factor when considering the ease of removal, the flexibility, and the amount of gel-forming liquid which is retained inside and therefore not used in the final gel itself.

The foam pad 11 represents a preferred aspect of the invention, and may be any resilient pad. This is placed beneath the membrane 10. When pressed, the pad 11 pushes the membrane 10 up against the rim around the bottom opening 14 of the gel enclosure, thus ensuring close contact between the membrane and the rim as well as uniform pressure along the full length of the rim. Any resilient material may be used; foam rubber is an example.

The support tray 12 serves to hold the wetted membrane 10 in place against the lower rim of the enclosure opening 14. The tray further serves to provide a stable base to support the enclosure in the vertical position, and to retain any excess solution draining off the wetted membrane, thereby keeping surrounding areas dry.

The support tray has a flat floor 20 upon which the foam pad 11 rests, and has an interior well 21 shaped to accommodate the bottom end of the gel enclosure 13. A pair of screws 22, 23 hold the gel enclosure in place, compressing it against a pair of resilient pads 24, 25 in the well interior. An alternative to the tray and screws shown in the drawing is a rigid flat plate held beneath the bottom opening 14 of the gel enclosure with the membrane 10 and foam pad 11 in between, similar to the way these elements are held by the tray. The plate may be held in place with upward tension by conventional securing means, such as rubber bands looped around hooks or similar structures on the sides of the gel enclosure.

A typical procedure by which the components shown in the FIGURE may be used is as follows. The membrane is first placed over the foam pad 11 in the bottom of the support tray 12, then wetted thoroughly with gel-forming liquid, or saturated with the liquid if the membrane is porous. The bottom end of the gel enclosure 13 is then inserted in the tray, pressed down for full contact between the membrane 10 and the rim around the lower opening 14, and secured in place by tightening the screws 22, 23. After the gel on the membrane has had sufficient time to set, the gel enclosure is filled from the top with gel-forming solution. In this disclosure, the term "fill" is intended to include partial filling. The entire gel slab is then permitted to set. Once this has occurred, the screws 22, 23 are loosened, and the gel enclosure 13 is removed from the support tray 12. The membrane 10 is then pulled off from the bottom of the gel enclosure, and the gel is ready for electrophoresis.

The procedure and structure may be modified to provide for bottom filling of the gel space when gradient gels are needed. This may be done, for example, by inserting a syringe needle (not shown) up through the membrane 10 from underneath, after the sealing gel on the membrane has set. Gel-forming solution of gradually changing concentration is then passed into the gel space through the syringe needle. Suitable parts in the foam pad 11 and the floor 20 of the support tray will permit passage of the needle.

The process and apparatus of the present invention are applicable to all gel-forming solutions used in electrophoresis, catalytic or otherwise, and preferably aqueous. Examples include solutions used to form aqueous gels, starch gels, and polyacrylamide gels. Catalytic gels are preferred, particularly polyacrylamide gels, using such catalysts as riboflavin, ammonium persulfate, tetramethylethylenediamine (TEMED) and betadimethylaminopropionitrile (DMAPN), either alone or in combinations. When catalyzed gels are used, it is preferred to use a higher concentration of catalysts in the solution applied to the membrane than in the solution used for formation of the bulk of the gel. Thus, the catalyst concentration in the solution applied to the membrane is preferably from about 1 to about 10 times the concentration in the solution added after the seal has been formed, preferably about 2 to about 8 times.

The present invention is applicable to enclosures for any gel configuration which require openings at opposite ends, including both tube gel enclosures and slab gel enclosures. Those with the greatest sealing problems are slab gel enclosures consisting of flat glass plates separated by spacer strips as shown in the FIGURE. A detailed description of such a gel sandwich arrangement and the clamps holding it together may be found in commonly owned co-pending application Ser. No. 06/782,756, filed Sept. 30, 1985. In large scale sandwich arrangements, alignment of the lower edges is difficult, and the capillary action sealing effect of the present invention is particularly useful.

The foregoing description is offered for illustrative purposes only. Numerous modifications, variations, and further embodiments beyond those described herein will be readily apparent to those skilled in the art, while still falling within the spirit and scope of the invention as claimed hereinbelow.

What is claimed is:
1. A method for casting a gel in a vertical gel enclosure having a bottom opening, said method comprising:
    (a) wetting a wettable membrane sized to cover said bottom opening with a first solution of a gel-forming substance;
    (b) holding said wetted membrane against said bottom opening until the gel-forming substance in said first solution sets to form a watertight seal across said bottom opening;
    (c) filling said gel enclosure with a second solution of said gel-forming substance;
    (d) setting the gel-forming substance in said second solution; and
    (e) removing said membrane from said bottom opening.
2. A method in accordance with claim 1 in which said wettable membrane is porous and step (a) comprises saturating said wettable membrane with said first solution.
3. A method in accordance with claim 1 in which said wettable membrane is paper and step (a) comprises saturating said paper with said first solution.
4. A method in accordance with claim 3 in which said paper is smooth paper having a water absorbency of about 1 to about 6 grams per 100 square centimeters and a wet strength of at least about 30 psi.
5. A method in accordance with claim 1 in which said gel-forming substance is comprised of a monomer and polymerization catalyst.
6. A method in accordance with claim 1 in which said gel-forming substance is comprised of a monomer and a polymerization catalyst, and the concentration of said polymerization catalyst in said first solution is from about one to about ten times the concentration of said polymerization catalyst in said second solution.
7. A method in accordance with claim 1 in which said gel-forming substance is comprised of a monomer and a polymerization catalyst, and the concentration of said polymerization catalyst in said first solution is from about two to about eight times the concentration of said polymerization catalyst in said second solution.
8. A method in accordance with claim 1 in which the gel formed by said gel-forming substance is polyacrylamide gel.
9. A method in accordance with claim 1 in which said first and second solutions are aqueous solutions.
10. A method for casting a polyacrylamide gel in a vertical gel enclosure having a bottom opening, said method comprising:
    (a) saturating a piece of smooth paper having a water absorbency of about 1 to about 6 grams per 100 square centimeters and a wet strength of at least about 25 psi, sized to cover said bottom opening, with a first aqueous solution of acrylamide monomer and a polymerization catalyst;
    (b) holding said saturated porous paper against said bottom opening until sufficient acrylamide monomer in said first solution polymerizes to form a watertight seal across said bottom opening;
    (c) filling said gel enclosure with a second aqueous solution of said acrylamide monomer and said polymerization catalyst;
    (d) polymerizing sufficient acrylamide monomer in said second solution to form a gel; and
    (e) removing said saturated porous paper from said bottom opening;

the concentration of said polymerization catalyst in said first aqueous solution being from about two times to about eight times the concentration of said polymerization catalyst in said second solution.

* * * * *